United States Patent [19]
Sami

[11] Patent Number: 5,972,617
[45] Date of Patent: Oct. 26, 1999

[54] OLIGONUCLEOTIDES AND METHODS FOR DETERMINING BEER SPOILAGE ABILITY OF LACTIC ACID BACTERIA

[75] Inventor: Manabu Sami, Moriya-machi, Japan

[73] Assignee: Asahi Breweries, Ltd., Tokyo, Japan

[21] Appl. No.: 09/108,837

[22] Filed: Jul. 2, 1998

[30] Foreign Application Priority Data

Jul. 7, 1997 [JP] Japan ..................................... 9-195268

[51] Int. Cl.$^6$ .............................. C12Q 1/68; C12P 19/34; C07H 21/04
[52] U.S. Cl. .......................... 435/6; 435/91.2; 536/24.32; 536/24.33
[58] Field of Search .............................. 435/6, 91.1, 91.2, 435/91.5; 536/24.3, 24.32, 24.33

[56] References Cited

U.S. PATENT DOCUMENTS 5,654,416  8/1997  Cummins ................................ 536/24.3

FOREIGN PATENT DOCUMENTS 10-14584  1/1998  Japan .

OTHER PUBLICATIONS

Sami et al. A new and rapid method for determination of beer–spoilage abillity of Lactobacilli. J. Am. Soc. Brew. Chem. 55(4):137–140., Oct. 1997.

Van Veen et al. Multidrug resistance mediated by a bacterial homolog of the human multidrug transporter MDR1. Proc. Natl. Acad. Sci. USA 93:10668–10672., Oct. 1996.

Sami et al. Hop–resistant *Lactobacillus brevis* contains a novel plasmid harboring a multidrug resistance–like gene. J. Ferm. Bioeng. 84(1):1–6., Sep. 1997.

Dowhanick and Russell. Advances in detection and identification methods applicable to the brewing industry. Beer and Wine Production, American Chemical Society, pp. 13–30., 1993.

embl155 database, accession No. AB005752, Jul. 1997.

embl155 database, accession No. U63741, Mar. 1997.

issued U.S. patents database, ID No. US–08–495–743–61, Aug. 1997.

*Primary Examiner*—Carla J. Myers
*Assistant Examiner*—Diana Johannsen
*Attorney, Agent, or Firm*—Browdy and Neimark

[57] ABSTRACT

The present invention provides oligonucleotides and a method for using same to confirm the presence or absence of a gene resistant to hop, which gene is an important factor for determining the beer-spoilage ability of lactic acid bacteria, and for rapidly assessing the likelihood for beer-spoilage by the presence or absence of lactic acid bacteria having a hop resistance gene, hopA.

4 Claims, No Drawings

SEQUENCE LISTING

<160> NUMBER OF SEQ ID NOS: 3

<210> SEQ ID NO 1
<211> LENGTH: 396
<212> TYPE: DNA
<213> ORGANISM: Lactobacillus brevis

<400> SEQUENCE: 1

| | | | | | |
|---|---|---|---|---|---|
| ggaccatccg | gcggtggcaa | atcaaccatt | tctagcttaa | ttgaacgttt | ttatgaacct | 60 |
| aacgagggca | gcatcacgat | tggcaatacc | aatattactg | atattcaact | tgccgattgg | 120 |
| cgccagcaaa | tcggcctggt | cggccaagac | gctgcgatca | tgtctggaac | gattcgttac | 180 |
| aatttaacct | atggtttgcc | ggggcatttt | tccgatgaac | agctttggca | tgtcttggaa | 240 |
| atggcttacg | caacgcaatt | tgtccagaag | atgcctcggg | gcttggacac | ggaagtcggt | 300 |
| gagcgtggag | tcaaggtatc | gggggggccaa | cgccaacgat | tggcgattgc | ccgggccttc | 360 |
| ctgcgtaatc | caaaaatatt | aatgttggat | gaagca | | | 396 |

<210> SEQ ID NO 2
<211> LENGTH: 19
<212> TYPE: DNA
<213> ORGANISM: Lactobacillus brevis

<400> SEQUENCE: 2
atccggcggt ggcaaatca                                                      19

<210> SEQ ID NO 3
<211> LENGTH: 18
<212> TYPE: DNA
<213> ORGANISM: Lactobacillus brevis

<400> SEQUENCE: 3
aatcgccaat cgttggcg                                                       18

OLIGONUCLEOTIDES AND METHODS FOR DETERMINING BEER SPOILAGE ABILITY OF LACTIC ACID BACTERIA

FIELD OF THE INVENTION

The present invention relates to oligonucleotides for judging beer-spoilage ability of lactic acid bacteria, which influences beer quality, and a method for judging the beer-spoilage ability with the oligonucleotides.

DESCRIPTION OF THE PRIOR ART

Beer is effective for controlling bacteria growth, because it contains alcohol, exhausts a carbon source, and has low pH and anaerobic conditions, and further it contains a hop having antibiotic activity. However, since a part of bacteria such as Lactobacillus genera is resistant to iso-α-acid, which is an ingredient in the hop, the bacteria mix in beer products and give the products turbidity.

Hitherto, the detection and judgement of bacteria, which influence the quality of beer, have been studied, for example, there are a method for detecting noxious bacteria in beer brewing by using antigen-antibody reaction (Japanese Patent Kokai Publication No. 57-59166), a method for detecting with monoclonal antibody for beer lactic acid bacteria (Japanese Patent Kokai Publication No. 06-105698), and a method comprising extracting DNA from lactic acid bacteria, conducting PCR with primers designated based on a particular sequence, amplifying the sequence and judging the presence or absence of lactic acid bacteria (Japanese Patent Kokai Publication No. 06-141899).

However, these methods are substantially methods for judging particular bacteria such as *Lactobacillus brevis*. For this reason, when *Lactobacillus brevis* not having beer-spoilage ability or the other bacteria having beer-spoilage ability are detected from beer or half-finished goods during beer production, there are problems that the beer-spoilage ability is judged in error, so that the judgement whether detected bacteria have beer-spoilage ability or not is difficult.

SUMMARY OF THE INVENTION

The present invention provides a method for judging rapidly whether detected lactic acid bacteria have beer-spoilage ability, by limiting a part of sequence of hop-resistance gene on a plasmid contained in *Lactobacillus brevis* of beer-spoilage lactic acid bacteria (Japanese Patent Kokai Publication No. 8-186621) and the nucleotide in the sequence, and conducting Polymerase Chain Reaction (PCR) with the nucleotide as the primer.

The present invention is an oligonucleotide for judging beer-spoilage ability of lactic acid bacteria, wherein it has a part of the nucleotide sequence or the whole nucleotide sequence of SEQ ID NO:1 or has the corresponding complementary sequence. Further, the present invention is an oligonucleotide for judging beer-spoilage ability of lactic acid bacteria, characterized in that a part of the nucleotide sequence is 5'-ATCCGGCGGTGGCAAATCA-3'(SEQ ID NO:2) or
5'-AATCGCCAATCGTTGGCG-3'(SEQ ID NO:3).

Preferably, the oligonucleotide of the present invention contains at least 10 continuous bases in above-mentioned nucleotide sequence.

The present invention is further a method for amplifying a target nucleotide, the above nucleotide sequence functionate as a primer of a polymerase chain reaction.

Moreover, the present invention is a method for judging beer-spoilage ability of lactic acid bacteria, said method comprising separating the nucleotide amplified by the above method by using electrophoresis, and judging the presence or absence of the nucleotide having a sequence to be recognized in the resulting nucleotide.

In the present invention, noticing the point that the most important factor for determining the beer-spoilage ability of lactic acid bacteria is hop resistance, since it is able to judge whether detected lactic acid bacteria have a hop-resistance gene or not by using gene sequences relating to the hop resistance, it is possible to foreknow rapidly the beer-spoilage ability of bacteria without confirmation by the bacteria growth in beer and the like.

DETAILED DESCRIPTION OF THE INVENTION

In the present invention, when lactic acid bacteria is detected from beer or the half-finished goods produced during beer production, the lactic acid bacteria are cultured. When lactic acid bacteria can grow, any culture mediums may be used, for example, the bacteria can increase in a MRS liquid medium. The culture conditions are anaerobic conditions at normal temperature to grow the lactic acid bacteria. The culture times are 1–2 days.

Cultured and increased bacteria are collected, and DNA is extracted by a well-known DNA extract method, for example a method of D. G. Anderson & L. L. Mackay et al. (App. Env. Microbiol. 46, p549, 1983) and is utilized in the judgement of the present invention.

To obtain two oligonucleotides for use as primers, a part of the sequence is determined from the hop-resistance gene described in Japanese Patent Application No. 8-186621, and it is synthesized chemically to obtain two primers opposite to each other. Especially, when the nucleotide sequences of SEQ ID NO:2 and 3 are used as primers for a polymerase chain reaction, if the lactic acid bacteria have the hop-resistance gene, DNA fragments of 342 bp are amplified by the judge method of the present invention.

Moreover, thermotolerance at 90° C. or more is enough for using the DNA polymerase. The temperature conditions of a PCR reaction are 90–98° C. in a thermal denaturation reaction for changing a double strand DNA into a one strand DNA, 37–68° C. in annealing of primers to a template DNA, and 50–75° C. in a chain elongation reaction to act polymerase. Using one cycle of these reactions, several tens cycle are conducted to amplify fragments of the hop-resistance gene.

After the PCR reaction, the reactant are separated by electrophoresis, nucleic acid stain with ethidium bromide or the like is conducted and the presence or absence of the amplification of DNA fragments is confirmed. When DNA fragments having a chain length specific for the primer designed, it is judged that the bacteria have the hop-resistance gene and beer-spoilage ability.

DESCRIPTION OF THE PREFERRED EMBODIMENTS

The present invention is described by working examples in the following. After Lactobacillus strains bacteria 95 strains described in Table 1, to be concrete, *Lactobacillus brevis, Lactobacillus casei, Lactobacillus plantarum, Lactobacillus lindneri, Lactobacillus collinoides* and the like were cultured in MRS liquid medium for 24 hours, DNA was extracted by a method of Anderson & MacKay.

Using the DNA as a template, and using two primers,

5'-ATCCGGCGGTGGCAAATCA-3'(SEQ ID NO:2) or
5'-AATCGCCAATCGTTGGCG-3'(SEQ ID NO:3),
which are based on SEQ ID NO:1

PCR was conducted with TAKARA Ex Taq and Program Temp Control System PC-800 (ASTEC).

As to the PCR method, well-known technique may be used (Science 230, p 13, 1995).

Five $\mu$l of the PCR product was separated by electrophoresis with agarose gel (NuSieve GTG, TAKARA) in which TAE buffer (0.04M, Tris-acetate, 0.01M EDTA, pH8.0) is dissolved to be 3%, and a set of MUPID minigel electrophoresis (ADVANCE CO.), and the PCR product was stained with ethidium bromide. As a molecular weight marker, $\phi$X174 DNA (TAKARA) cut with HincII was used.

The temperature conditions of the judge method in the present invention are 94° C. for 3 minutes as one cycle, 98° C. for 30 seconds and 55° C. for one minute and 72° C. for 0.5 minutes as 25 cycles.

Moreover, as to 95 strains described in Table 1, beer-spoilage ability was tested by the following steps.

Firstly, after culturing in a MRS liquid medium, each bacterium was inoculated to be $10^5$ cells/ml to degassed beer of bitterness value 20, which is adjusted to pH4.6, and cultured at 25° C. for two months under anaerobic conditions. After culturing, the strain, which was recognized the presence of beer-spoilage ability by the eye, was judged that it has beer-spoilage ability.

As shown in the results of Table 1, by the judge method (horA-PCR) of the present invention, the strains that the specific amplification of 342 bp DNA fragments was observed were 61 strains in 95 strains, and the strains that the specific amplification was not observed were 34 strains. In fact, compared with the results that turbidity was recognized after inoculating the bacteria to beer of pH4.6, two strains not having beer-spoilage ability were judged as positive by a horA-PCR method, while one strain having beer-spoilage ability was judged as negative by the horA-PCR method. Accordingly, it was recognized that the method was very accurate.

TABLE 1

| Bacterium Species | Test Bacterium No. | Judgement by the Present Invention | Beer-spoilage ability |
|---|---|---|---|
| L.brevis | 1 | + | + |
| L.brevis | 2 | + | + |
| L.brevis | 3 | + | + |
| L.brevis | 4 | + | + |
| L.brevis | 5 | + | + |
| L.brevis | 6 | + | + |
| L.brevis | 7 | + | + |
| L.brevis | 8 | + | + |
| L.brevis | 9 | + | + |
| L.brevis | 10 | + | + |
| L.brevis | 11 | + | + |
| L.brevis | 12 | + | + |
| L.brevis | 13 | + | + |
| L.brevis | 14 | + | + |
| L.brevis | 15 | + | + |
| L.brevis | 16 | + | + |
| L.brevis | 17 | + | + |
| L.brevis | 18 | + | + |
| L.brevis | 19 | + | + |
| L.brevis | 20 | + | + |
| L.brevis | 21 | + | + |
| L.brevis | 22 | + | + |
| L.brevis | 23 | + | + |
| L.brevis | 24 | + | + |
| L.brevis | 25 | − | − |
| L.brevis | 26 | − | − |
| L.brevis | 27 | − | − |
| L.brevis | 28 | − | − |
| L.brevis | 29 | + | + |

TABLE 1-continued

| Bacterium Species | Test Bacterium No. | Judgement by the Present Invention | Beer-spoilage ability |
|---|---|---|---|
| L.brevis | 30 | + | + |
| L.brevis | 31 | + | + |
| L.brevis | 32 | + | + |
| L.brevis | 33 | + | + |
| L.brevis | 34 | + | + |
| L.brevis | 35 | + | + |
| L.brevis | 36 | + | + |
| L.brevis | 37 | + | + |
| L.brevis | 38 | + | + |
| L.brevis | 39 | + | + |
| L.brevis | 40 | + | + |
| L.brevis | 41 | + | + |
| L.brevis | 42 | + | + |
| L.brevis | 43 | + | + |
| L.brevis | 44 | − | − |
| L.brevis | 45 | + | + |
| L.brevis | 46 | + | + |
| L.brevis | 47 | + | + |
| L.casei | 48 | − | − |
| L.casei | 49 | − | − |
| L.casei | 50 | − | − |
| L.casei | 51 | + | + |
| L.casei | 52 | − | − |
| L.casei | 53 | − | − |
| L.casei | 54 | − | − |
| L.casei | 55 | − | − |
| L.casei | 56 | − | − |
| L.casei | 57 | − | − |
| L.casei | 58 | − | − |
| L.plantarum | 59 | − | − |
| L.plantarum | 60 | − | − |
| L.plantarum | 61 | − | − |
| L.plantarum | 62 | − | − |
| L.lindneri | 63 | + | + |
| L.lindneri | 64 | + | + |
| L.lindneri | 65 | + | + |
| L.collinoides | 66 | − | − |
| L.collinoides | 67 | − | − |
| L.collinoides | 68 | − | − |
| L.delbrueckii | 69 | − | − |
| L.fermentum | 70 | − | − |
| L.rhamnosus | 71 | − | − |
| L.sp. | 72 | − | − |
| L.sp. | 73 | − | − |
| L.sp. | 74 | − | − |
| L.sp. | 75 | − | − |
| L.sp. | 76 | + | + |
| L.sp. | 77 | + | + |
| L.sp. | 78 | + | + |
| L.sp. | 79 | + | + |
| L.sp. | 80 | + | + |
| L.sp. | 81 | + | + |
| L.sp. | 82 | + | + |
| L.sp. | 83 | + | + |
| L.sp. | 84 | + | + |
| L.sp. | 85 | − | − |
| L.sp. | 86 | − | − |
| L.sp. | 87 | − | − |
| L.sp. | 88 | − | − |
| L.sp. | 89 | + | + |
| L.sp. | 90 | + | + |
| L.sp. | 91 | + | + |
| L.sp. | 92 | + | + |

Merits of the invention are as follows. When bacteria having a high possibility of beer-spoilage ability, such as *Lactobacillus brevis* and *Lactobacillus lindneri,* are judged as beer-spoilage bacteria by many conventional identifiable methods, there are many error judges. When beer-spoilage ability is further actually tested by inoculation of bacteria, it takes several weeks to several months.

However, by using the oligonucleotide of the present invention and the method for judging beer-spoilage ability with the oligonucleotide, it is possible to accurately judge the beer-spoilage ability in a few hours.

I claim:

1. A pair of oligonucleotides for determining the beer-spoilage ability of lactic acid bacteria, wherein one oligonucleotide of said pair of oligonucleotides comprises the nucleotide sequence of SEQ ID NO:2 and the other oligonucleotide of said pair of oligonucleotides comprises the nucleotide sequence of SEQ ID NO:3.

2. The pair of oligonucleotides according to claim 1, wherein one oligonucleotide of said pair consists of the nucleotide sequence of SEQ ID NO:2 and the other oligonucleotide of said pair consists of the nucleotide sequence of SEQ ID NO:3.

3. A method for determining the beer-spoilage ability of lactic acid bacteria, comprising:

extracting DNA from cultured microorganisms of the Lactobacillus genus of lactic acid bacteria;

amplifying from the extracted DNA fragments encoding the hop resistance gene horA by PCR using the pair of oligonucleotides according to claim 1; and detecting the presence of DNA fragments encoding horA by gel electrophoresis as indicative of beer-spoilage ability of the cultured microorganisms of the Lactobacillus genus of lactic acid bacteria.

4. The method according to claim 3, wherein the DNA is extracted from Lactobacillus cultured from beer or half-finished goods during beer production.

* * * * *